US010039472B2

(12) United States Patent
Aina-Mumuney et al.

(10) Patent No.: US 10,039,472 B2
(45) Date of Patent: Aug. 7, 2018

(54) PRETERM LABOR MONITOR

(71) Applicants: Abimbola Aina-Mumuney, Baltimore, MD (US); Deepika Sagaram, North Wales, PA (US); Christopher B. Courville, Bristol (GB); Karin Hwang, Ontario, CA (US); Rose Yi Huang, Brooklyn, NY (US); Karin J. Blakemore, Baltimore, MD (US); Soumyadipta Acharya, Baltimore, MD (US)

(72) Inventors: Abimbola Aina-Mumuney, Baltimore, MD (US); Deepika Sagaram, Providence, RI (US); Christopher B. Courville, Bristol (GB); Karin Hwang, Ontario, CA (US); Rose Yi Huang, Brooklyn, NY (US); Karin J. Blakemore, Baltimore, MD (US); Sung J. Sunwoo, Laurel, MD (US); Soumyadipta Acharya, Baltimore, MD (US)

( * ) Notice: Subject to any disclaimer, the term of this patent is extended or adjusted under 35 U.S.C. 154(b) by 0 days.

(21) Appl. No.: 14/495,433

(22) Filed: Sep. 24, 2014

(65) Prior Publication Data
US 2015/0031976 A1     Jan. 29, 2015

Related U.S. Application Data

(62) Division of application No. 13/580,046, filed as application No. PCT/US2011/025494 on Feb. 18, 2011, now Pat. No. 8,874,183.
(Continued)

(51) Int. Cl.
*A61B 5/0488* (2006.01)
*A61B 5/0492* (2006.01)
(Continued)

(52) U.S. Cl.
CPC .......... *A61B 5/0492* (2013.01); *A61B 5/0084* (2013.01); *A61B 5/04* (2013.01);
(Continued)

(58) Field of Classification Search
CPC ...... A61B 5/0492; A61B 5/435; A61B 5/4356
See application file for complete search history.

(56) References Cited

U.S. PATENT DOCUMENTS 3,945,373 A    3/1976 Tweed et al.
4,577,640 A    3/1986 Hofmeister
(Continued)

OTHER PUBLICATIONS

PCT/US2011/025494: International Search Report and Written Opinion mailed Sep. 20, 2011.
(Continued)

*Primary Examiner* — Lee S Cohen
(74) *Attorney, Agent, or Firm* — Venable LLP; Henry J. Daley; Laura G. Remus

(57) ABSTRACT

A system, method and apparatus for monitoring uterine and/or cervical activity indicative of labor in a patient. The system includes a medical device and a data processor in communication with the medical device. The medical device includes a structural component, a first electrode attached to the structural component, and a second electrode attached to the structural component. The structural component is structured to be in contact with a cervical surface and a vaginal surface of the patient, such that said first electrode is in electrical contact with said cervical surface and said second electrode is in electrical contact with said vaginal surface. The first electrode is adapted to receive an electrical activity of the cervical surface and the second electrode is adapted to receive an electrical activity of the uterus through the vaginal surface. The data processor is adapted to process the electrical activity of the electrodes to detect contractions on a surface of the patient indicative of labor.

8 Claims, 17 Drawing Sheets

Related U.S. Application Data

(60) Provisional application No. 61/305,616, filed on Feb. 18, 2010.

(51) Int. Cl.
*A61B 5/00* (2006.01)
*A61B 5/107* (2006.01)
*A61B 5/04* (2006.01)

(52) U.S. Cl.
CPC ........ *A61B 5/04882* (2013.01); *A61B 5/1076* (2013.01); *A61B 5/435* (2013.01); *A61B 5/4356* (2013.01); *A61B 5/6882* (2013.01)

(56) References Cited

U.S. PATENT DOCUMENTS

| | | |
|---|---|---|
| 5,406,961 A | 4/1995 | Artal |
| 5,522,877 A | 6/1996 | Garfield et al. |
| 5,623,939 A | 4/1997 | Garfield |
| 6,423,000 B1 | 7/2002 | Berry |
| 7,828,753 B2 | 11/2010 | Euliano, II et al. |
| 7,831,302 B2 | 11/2010 | Thomas |
| 7,853,319 B2 | 12/2010 | Davies |
| 2002/0193701 A1 | 12/2002 | Simpson et al. |
| 2004/0152997 A1 | 8/2004 | Davies |
| 2007/0255184 A1 | 11/2007 | Shennib |
| 2008/0154109 A1 | 6/2008 | Sogade |
| 2008/0171950 A1 | 7/2008 | Franco |
| 2009/0171234 A1 | 7/2009 | Gurewitsch et al. |
| 2009/0299212 A1 | 12/2009 | Principe et al. |
| 2009/0318914 A1* | 12/2009 | Utley ............. A61B 18/1206 606/33 |
| 2011/0190652 A1 | 8/2011 | Fink et al. |

OTHER PUBLICATIONS

PCT/US2011/025494: International Search Report and Written Opinion mailed Nov. 13, 2012.

\* cited by examiner

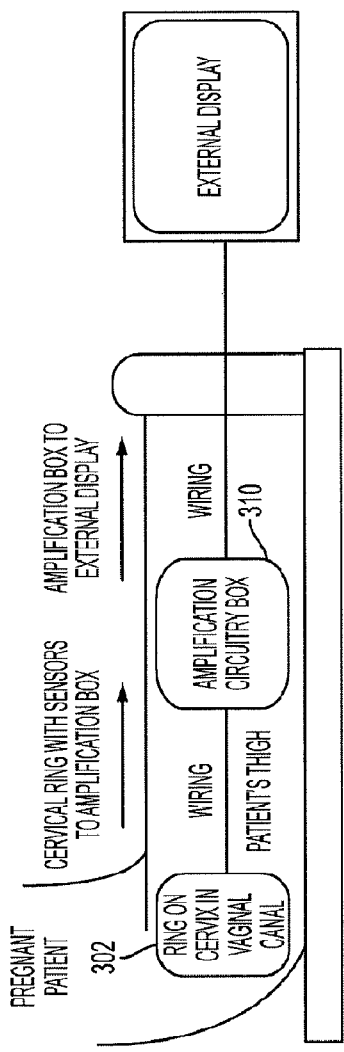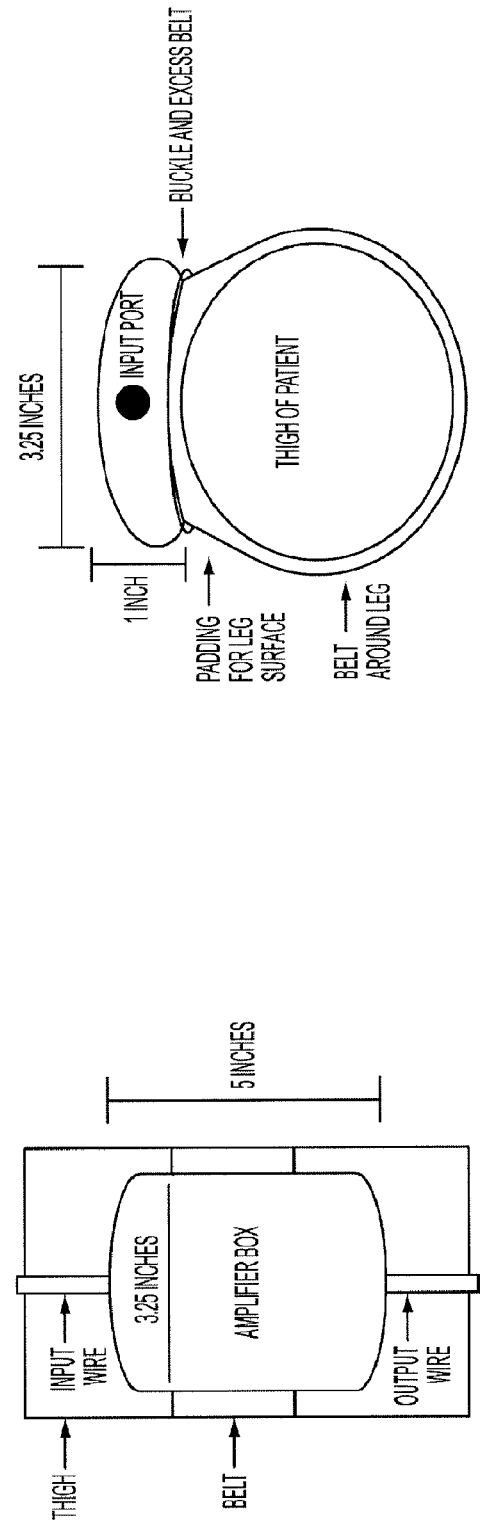

PRETERM LABOR MONITOR

CROSS-REFERENCE OF RELATED APPLICATION

This application is a divisional of U.S. patent application Ser. No. 13/580,046, filed Aug. 20, 2012, which issued as U.S. Pat. No. 8,874,183 on Oct. 28, 2014 and is a National Stage Application of PCT/US2011/025494, filed Feb. 18, 2011, which designates the United States and claims the priority of U.S. Provisional Application No. 61/305,616 filed Feb. 18, 2010, the entire contents of all of which are hereby incorporated by reference.

BACKGROUND

1. Field of Invention

The field of the currently claimed embodiments of this invention relates to systems and methods for measuring and monitoring uterine cervical activity indicative of labor.

2. Discussion of Related Art

Despite recent technological medical breakthroughs, the issue of diagnosing preterm labor has continued to plague the obstetric community. In order to fully understand the gravity of this need, it is important to recognize the regrettable outcomes and heavy costs related to preterm birth. Preterm births lead to 70% percent of neonatal morbidity and mortality, and cost the United States over $26.2 billion in 2005 alone. Currently there is no way of accurately detecting preterm labor, which often leads to preterm birth. Current detection methods, such as the commonly used tocodynamometer, lack the ability to detect critical cervical changes and uterine activity and/or contractions at early gestational ages. This prevents timely diagnosis and treatment of preterm labor. A method and device that detects preterm labor early in its course in patients is currently lacking.

Term delivery occurs between 37-42 weeks of gestation, whereas preterm delivery occurs between 20-37 weeks of gestation. Preterm delivery does not allow the fetus enough time to develop within the womb, resulting in severe short and long-term health issues for the neonate.

The unfortunate consequences of preterm delivery have encouraged the obstetric community to increase monitoring on those pregnancies with predetermined risk factors for preterm labor. These predetermined characteristics include factors such as extremes in maternal age (under 17 or over 35) and a history of preterm birth. Of the over 4 million births in the US each year, around 680,000 of those are considered at risk for preterm birth. These patients are monitored closely and required to make clinical visits as often as once a week. The main risk factors include: extremes in maternal age (<17 or >35); low socioeconomic status; stressful life situations; low weight gain; infection; cervical abnormalities or trauma; and history of preterm labor and birth.

The results of preterm delivery directly correlate to vast increases in medical costs. While current medical costs of term birth in the US average around $2,800 USD, the average cost of preterm delivery is $41,000 USD. This disparity in costs comprises a portion of the $26.2 billion dollars spent on preterm deliveries in 2005 alone.

All of the current methods employed to screen for preterm labor are ineffective, insufficient, or inaccurate. The tocodynamometer, used to detect contractions from the abdominal surface, is often unable to detect contractions and cervical changes at an early gestational age. Transvaginal ultrasound, while able to detect cervical changes even at very early gestational ages, cannot usually detect the contractions that are often present before these changes are evident. Symptomatic monitoring is insufficient because patients are most often not evaluated until the time for meaningful intervention has passed. Other tests such as infection screening only monitor one potential mechanism for labor initiation. Fetal fibronectin testing, while modestly accurate at predicting preterm labor, has a much higher negative predictive value.

Even with increased surveillance, the failings of current methods have led to an annual preterm birth rate of twelve percent in the United States. Failure to detect preterm labor early in its course means that by the time cervical changes have truly manifested, delivery can only be delayed by a few days. Additional difficulty arises in striking a balance between avoiding unnecessary intervention and making timely diagnosis and treatment. Therefore, there is a need for a device that accurately detects early signs of preterm labor in patients.

SUMMARY

A medical device for monitoring uterine and/or cervical activity indicative of labor in a patient, according to an embodiment of the current invention, includes a structural component, a first electrode attached to the structural component and a second electrode attached to the structural component. The structural component is structured to be in contact with a cervical surface and a vaginal surface of the patient, such that the first electrode is in electrical contact with the cervical surface and the second electrode is in electrical contact with the vaginal surface. The first electrode is adapted to receive an electrical activity of the cervical surface and the second electrode is adapted to receive an electrical activity of the uterus through the vaginal surface.

A system for monitoring uterine and/or cervical activity indicative of labor in a patient, according to an embodiment of the current invention, includes a medical device and a data processor in communication with the medical device. The medical device includes a structural component, a first electrode attached to the structural component and a second electrode attached to the structural component. The structural component is structured to be in contact with a cervical surface and a vaginal surface of the patient, such that the first electrode is in electrical contact with the cervical surface and the second electrode is in electrical contact with the vaginal surface. The first electrode is adapted to receive an electrical activity of the cervical surface and the second electrode is adapted to receive an electrical activity of the uterus through the vaginal surface. The data processor is adapted to process the electrical activity of the first and second electrodes to detect contractions on at least one surface of the patient indicative of labor.

A method of monitoring uterine and/or cervical activity indicative of labor in a patient, according to an embodiment of the current invention, includes the following steps: positioning a medical device within a patient, where a structural component of the medical device is structured to be in contact with a cervical surface and a vaginal surface of the patient; receiving an electrical activity of the cervical surface using a first electrode attached to the structural component, where the first electrode is in electrical contact with the cervical surface; receiving an electrical activity of the uterus through the vaginal surface using a second electrode attached to the structural component, where the second electrode is in electrical contact with the vaginal surface;

and processing the electrical activity of the cervical and vaginal surfaces using a data processor in communication with the medical device to detect contractions of the uterus indicative of labor.

BRIEF DESCRIPTION OF THE DRAWINGS

Further objectives and advantages will become apparent from a consideration of the description, drawings, and examples.

FIG. 7B is a block diagram of the system operation, in accordance with at least some embodiments of the present invention.

FIG. 7C is a schematic illustration of a top view of an amplifier box attachable to a patient, in accordance with at least some embodiments of the present invention.

FIG. 7D is a schematic illustration of a side view of an amplifier box attachable to a patient, in accordance with at least some embodiments of the present invention.

DETAILED DESCRIPTION

Some embodiments of the current invention are discussed in detail below. In describing embodiments, specific terminology is employed for the sake of clarity. However, the invention is not intended to be limited to the specific terminology so selected. A person skilled in the relevant art will recognize that other equivalent components can be employed and other methods developed without departing from the broad concepts of the current invention. All references cited anywhere in this specification, including the Background and Detailed Description sections, are incorporated by reference as if each had been individually incorporated.

Figure 1:
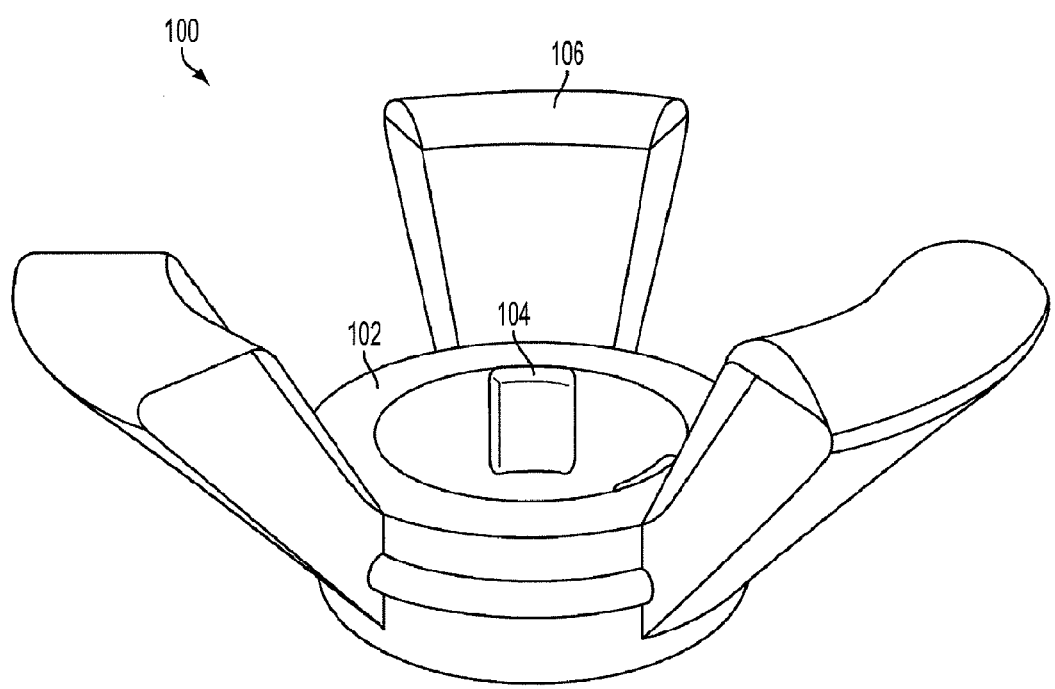
FIG. 1 is a schematic illustration of a top perspective view of a medical device, in accordance with at least some embodiments of the present invention.
Figure 2A:
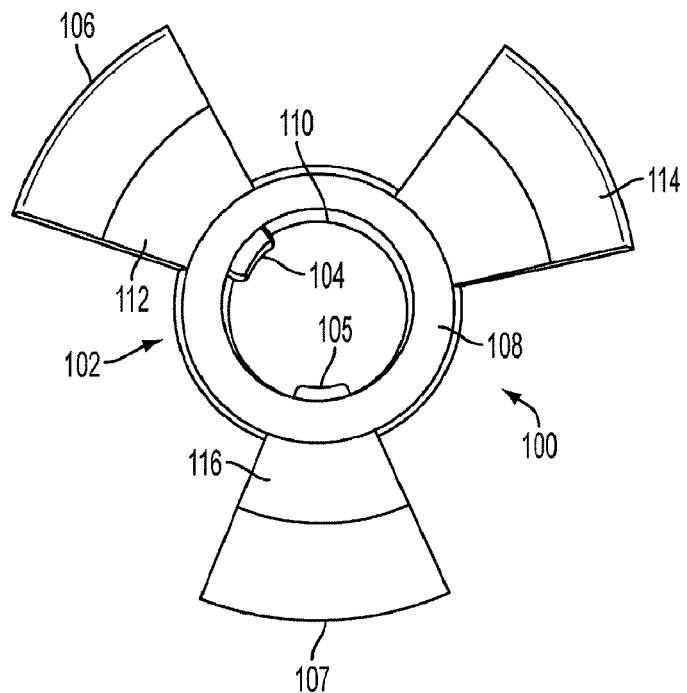
FIGS. 2A-2D are various schematic illustrations of the medical device, in accordance with at least some embodiments of the present invention.
Figure 2B:
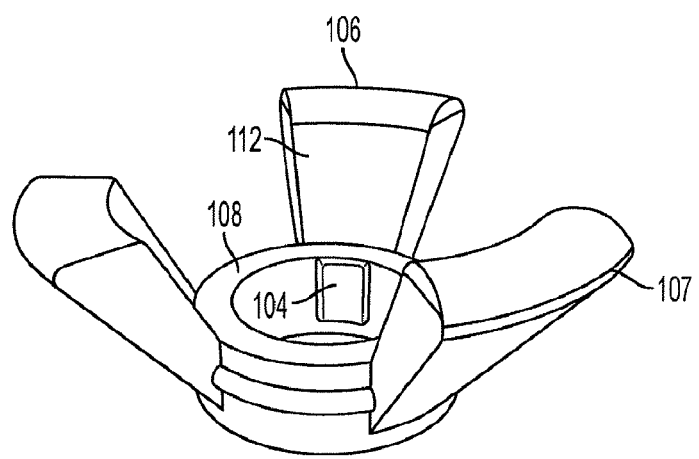
Figure 2C:
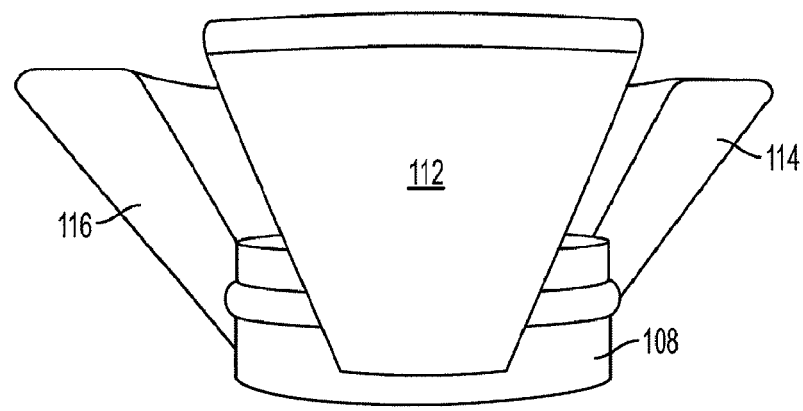
Figure 2D:
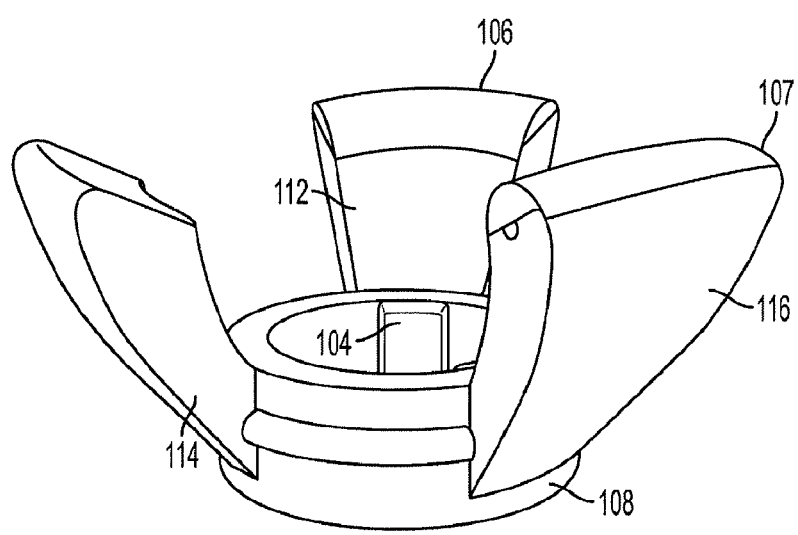

FIG. 1 is a schematic illustration of a top perspective view of a medical device 100, in accordance with at least some embodiments of the present invention. The medical device 100 is adapted to monitor uterine and/or cervical activity indicative of labor in a patient. The medical device 100 includes a structural component 102, as well as a first electrode 104 and a second electrode 106 each attached to the structural component 102. The structural component 102 is structured to be in contact with a cervical surface and a vaginal surface of a medical patient (See FIGS. 3 and 4), such that the first electrode 104 is in electrical contact with the cervical surface and the second electrode 106 is in electrical contact with the vaginal surface. The first electrode 104 is adapted to receive an electrical activity of the cervical surface and the second electrode 106 is adapted to receive an electrical activity of the uterus through the vaginal surface.

Figure 11:
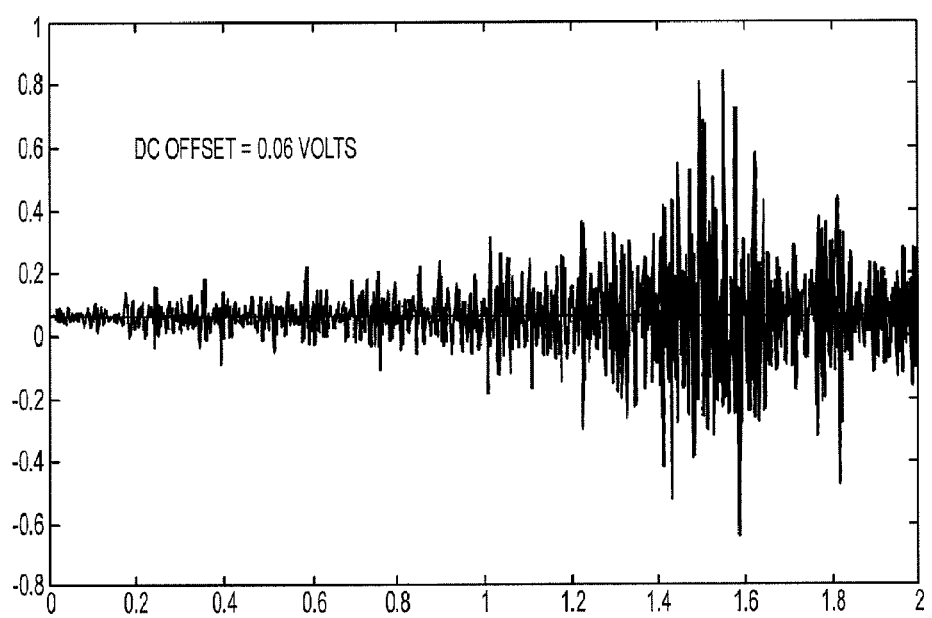
FIG. 11 shows a chart illustrating the measurement of electrical activity of an example muscle using electromyography, in accordance with at least some embodiments of the present invention.

According to one embodiment, the first and second electrodes 104, 106 may comprise electromyography electrodes (hereinafter referred to as "EMG electrodes"). Electromyography (EMG) is a technique used for evaluating and recording electrical activity produced by muscles, for example the smooth muscle of the cervix, uterus and/or abdomen of a pregnant patient. (See FIG. 11, a chart illustrating the electrical activity of an example muscle using EMG). Alternatively, the device may detect cervical and/or uterine activity using other types of biocompatible sensors.

In another embodiment, the first electrode 104 may receive the electrical activity of the cervical surface with respect to a reference signal and the second electrode 106 may receive the electrical activity of the uterus through the vaginal surface with respect to a reference signal. The reference signal may be, for example, the electrical activity taken from the inner thigh of the patient.

FIGS. 2A-2D are various schematic illustrations of the medical device 100, in accordance with at least some embodiments of the present invention. As shown in the top view of FIG. 2A, the structural component 102 may include an elastic ring 108 defining a hollow center that is suitable to be arranged in contact with the cervical surface (See FIGS. 3 and 4). One or more electrodes 104, 105 may be positioned on an interior portion 110 of the elastic ring 108.

According to a further embodiment, the structural component 102 may also include a projecting portion 112 coupled to and/or integral with the elastic ring 108. The projecting portion 112 may be structured to be arranged in contact with the vaginal surface of the patient. The second electrode 106 may be positioned on the projecting portion 112.

According to another embodiment, the structural component 102 may include a plurality of projecting portions 112, 114, 116 coupled to and/or integral with the elastic ring 108. In this embodiment, electrodes 106, 107 may be coupled to each of the projecting portions.

Figure 3:
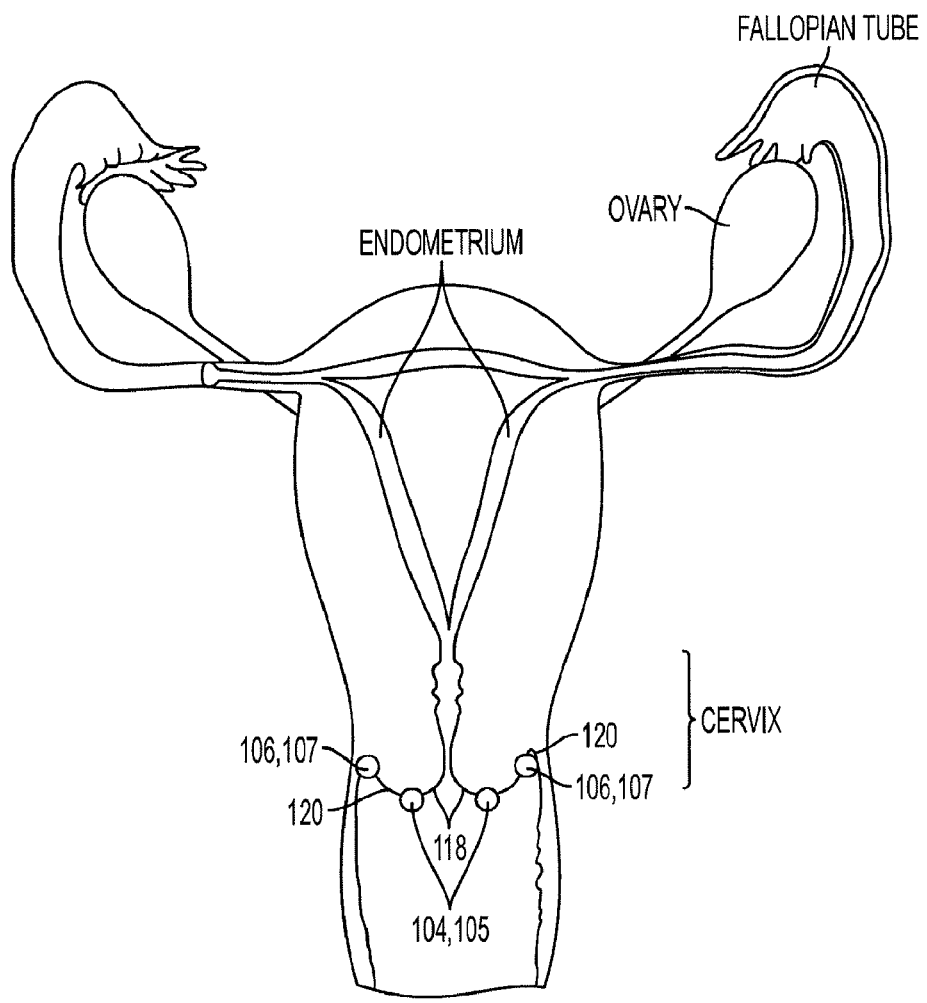
FIG. 3 is schematic illustration of the placement of the electrodes on the patient, in accordance with at least some embodiments of the present invention.

FIG. 3 is schematic illustration to explain the desired placement of the electrodes on the patient, in accordance with at least some embodiments of the present invention. FIG. 3 shows the patient's reproductive tract, including (from the top) the ovaries, the fallopian tubes, the endometrium (i.e. the inner membrane of the uterus), the cervix and the vagina of the patient. In this embodiment, two electrodes 104, 105 are in electrical contact with the cervical surface 118 of the patient and two electrodes 106, 107 are in electrical contact with the vaginal surface 120 of the patient.

Figure 4:
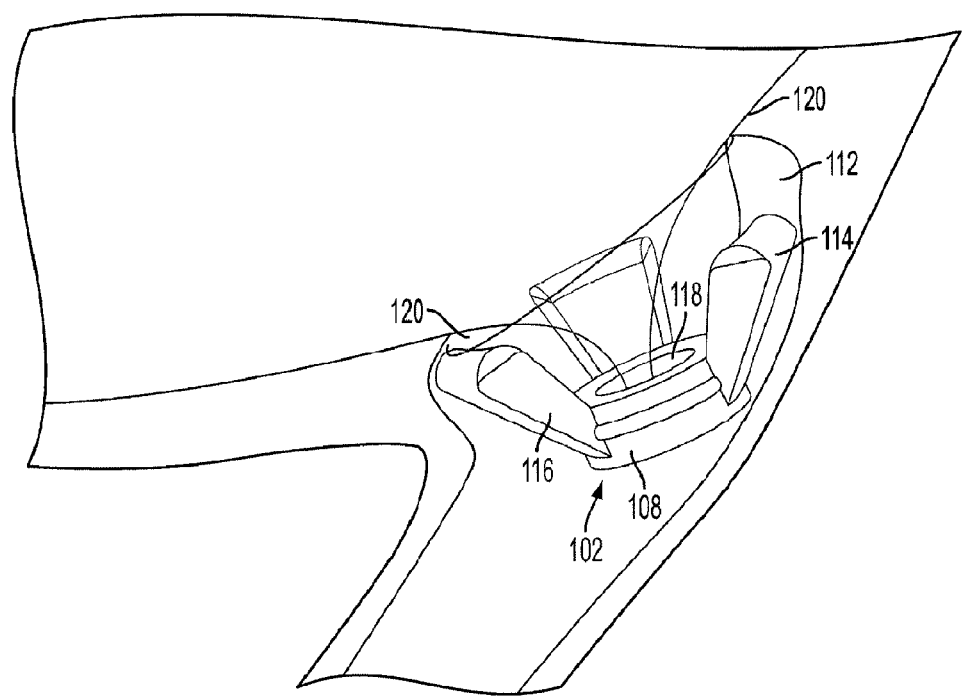
FIG. 4 is a schematic illustration of the placement of the medical device within the patient, in accordance with at least some embodiments of the present invention.

FIG. 4 is a schematic illustration of the placement of the medical device 100 within the patient, in accordance with at least some embodiments of the present invention. As shown, the structural component 102 is completely positioned within the reproductive tract of the patient. The elastic ring 108 of the medical device 100 is positioned relative to a cervical surface 118 of the patient and the projecting portions 112, 114, 116 are positioned relative to a vaginal surface 120 of the patient.

Figure 5:
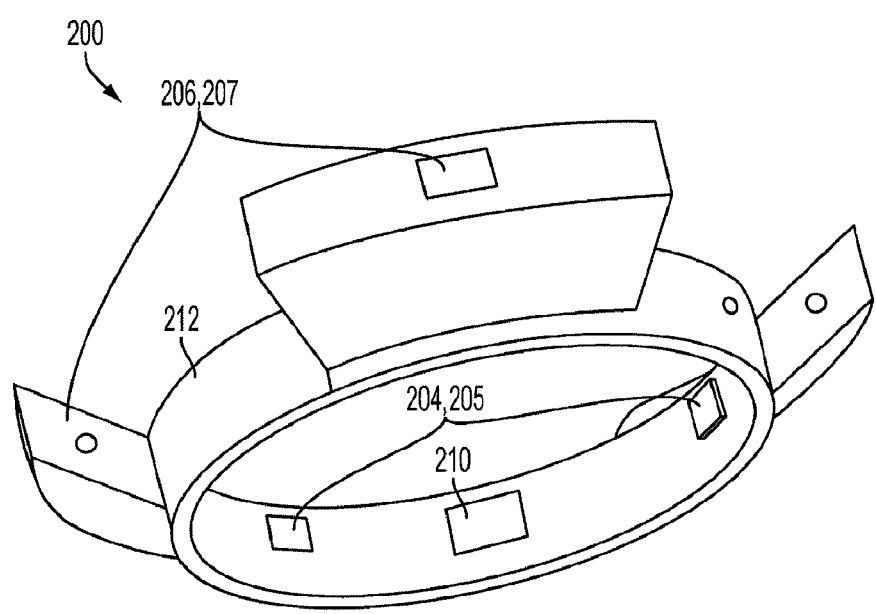
FIG. 5 is a schematic illustration of a bottom perspective view of the medical device, in accordance with at least some embodiments of the present invention.

FIG. 5 is a schematic illustration of a bottom perspective view of the medical device 200, in accordance with at least some embodiments of the present invention. Similar to the embodiments described above, the medical device 200 may include electrodes 204, 205 in electrical contact with the cervical surface 118 of the patient and electrodes 206, 207 in electrical contact with the vaginal surface 120 of the patient. Different numbers and placements of the electrodes are also possible.

According to one embodiment, a stretch sensor 212 (also referred to as a dilatation sensor or stretch gauge) may be attached to the medical device 200. For example, the stretch sensor 212 may be attached along the exterior portion of the elastic ring 108 (See FIGS. 2A-2D). The stretch sensor 212 may be adapted to detect a change in resistance of the cervical surface 118 of the patient. In one embodiment, the stretch sensor may be a wire positioned along the exterior circumference of the elastic ring that carries a current. The stretch sensor 212 may measure physical changes from the stretching of two leads positioned at either end of the wire.

Figure 6A:
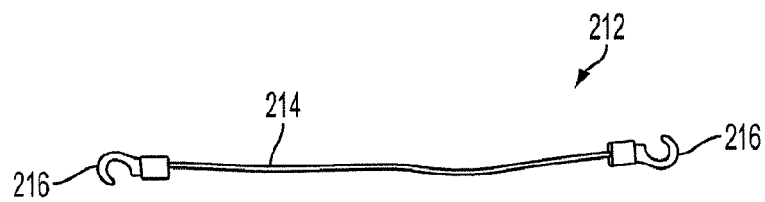
FIG. 6A is a schematic illustration of the stretch sensor that can be adapted for use, in accordance with at least some embodiments of the present invention.
Figure 6B:
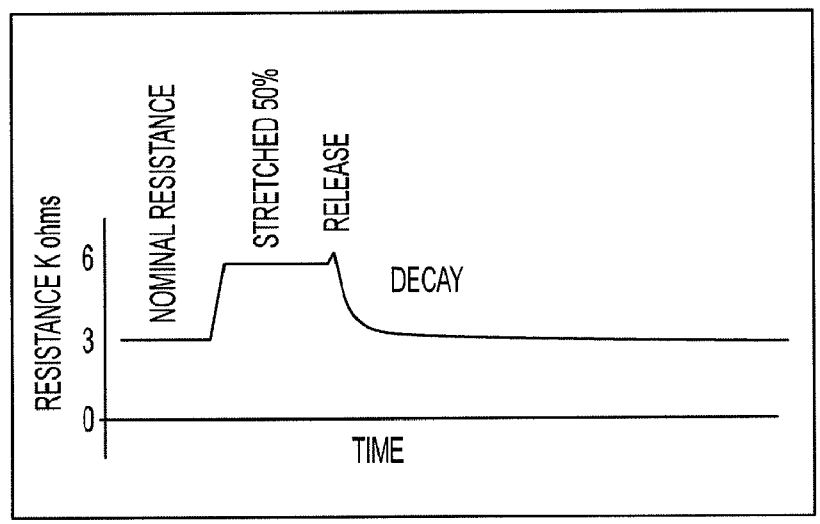
FIG. 6B is a chart illustrating the approximate resistive response of an example of stretch material, in accordance with at least some embodiments of the present invention.

FIG. 6A is a schematic illustration of the stretch sensor 212 that can be adapted for use, in accordance with at least some embodiments of the present invention, and FIG. 6B is a chart illustrating the approximate resistive response of an example of a stretch material. According to one embodiment, the stretch sensor 212 may be a flexible component that changes resistance when stretched. When relaxed the sensor material may have a nominal resistance measured in ohms per linear inch. When stretched, the sensor's resistance may gradually increase. When the stretch sensor 212 is stretched to 50%, its resistance will approximately double. The stretch sensor 212 may measure stretch, displacement and force. According to one example, the stretch sensor 212 may be a flexible cylindrical cord 214 with spade or ring terminals 216 at each end. In the present application, the stretch sensor 212 may measure the dilatation of the cervical surface 118 of the patient.

According to another embodiment, as shown in FIG. 5, a light sensor 210 (also referred to as an effacement sensor) may be attached to the medical device 200. For example, the light sensor 210 may be attached along the interior portion 110 of the elastic ring 108 (See FIGS. 2A-2D). The light sensor 210 may be adapted to measure changes in light reflectance and/or light transmission on the cervical surface 118 of the patient. The light sensor 210 may be one or more diodes for transmitting and/or receiving light. The term "light" is intended to have a broad meaning to include both visible and non-visible regions of the spectrum. For example, infrared, visible light and/or ultraviolet light emitting diodes (LEDs) can be used, depending on the particular embodiment. Optical diodes can be used to both transmit and receive in some embodiments, or there can be separate transmitters and receivers in other embodiments.

Figure 7A:
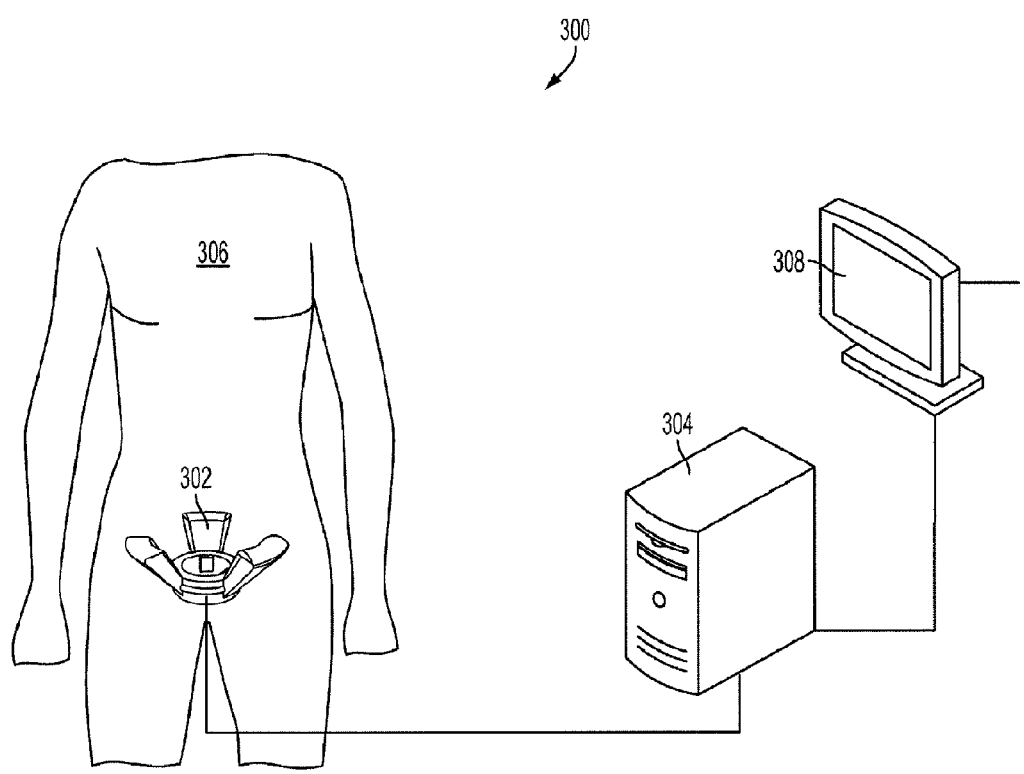
FIG. 7A is a schematic illustration of a system for monitoring uterine and/or cervical activity indicative of labor in a patient, in accordance with at least some embodiments of the present invention.

FIG. 7A is a schematic illustration of a system 300 for monitoring uterine and/or cervical activity indicative of labor in a patient, in accordance with at least some embodiments of the present invention. The system may include software to perform amplification, filtering, and normalizing raw data and an external display for clinicians to examine processed data.

According to one embodiment, the system 300 may include a medical device 302 and a data processor 304 in communication with the medical device 302. The medical device 302 can be any one of the previous embodiments (See medical devices 100, 200 above) or a different embodiment. The data processor 304 may be adapted to process the electrical activity of one or more electrodes in electrical connection with a cervical and/or vaginal surface to detect contractions on at least one surface of the patient 306 indicative of labor. As described below, the data processor may measure the voltage difference and/or electrical potential difference between electrodes. The electrodes may be in unipolar, bi-polar or multi-polar arrangement. The data processor may offer real-time monitoring and signal processing. As discussed below, the system 300 may further include an external display 308 in communication with the data processor 304 to display information to a physician, patient or third party.

According to one embodiment, the data processor 304 may compare the electrical potential of the cervical surface 118 relative to the vaginal surface 120 to determine the uterine activity of the patient. In this embodiment, the medical device 100 may require a bi-polar arrangement, meaning only two electrodes. A first electrode 104 may be in direct electrical contact with and receive the electrical activity of the cervical surface 118. A second electrode 106 may be in direct electrical contact with and receive the electrical activity of the uterus through the vaginal surface 120 of a patient 306.

According to another embodiment, the data processor 304 may compare the electrical potential between at least two different locations of the cervical surface 118 to determine the uterine activity of the patient. In this embodiment, at least two electrodes 104, 105 may be attached to the elastic ring of the medical device 302 to receive the electrical activity from at least two different locations of the cervical surface 118. The data processor 304 may then compare the electrical potential between the two different locations.

According to a further embodiment, the data processor may compare the electrical potential between at least two different locations of the vaginal surface 120 to determine the uterine activity of the patient. In this embodiment, at least one electrode 106, 107 is positioned on each of each projecting portion 112, 116 to receive electrical activity from at least two different locations of the vaginal surface 120. The data processor 304 may then compare the electrical potential between the two different locations.

According to one embodiment, a stretch sensor 212 may be attached to the medical device 300 to detect changes in resistance in the cervical surface 118 of the patient. Alternatively, or additionally, a light sensor 210 may be attached to the medical device 300 to measure light reflectance on the cervical surface of the patient. The data processor 304 may then be adapted to process the change in resistance and/or the reflectance of the cervical surface 118 to detect contractions of the uterus indicative of labor.

FIG. 7B is a block diagram of the system operation, in accordance with at least some embodiments of the present invention. According to this embodiment, an amplifier box 310 may be in communication with the medical device 302 via hardwire or wireless connection. The amplifier box 310 may be in further communication with a data processor 304 having an external display 308. As discussed below, the amplifier box 310 may include circuitry adapted to receive signals from each of the electrodes and sensors of the medical device 302, to amplify and reduce noise in the signals, and to output the signals to the data processor 304.

FIGS. 7C and 7D are schematic illustrations of an amplifier box attachable to a patient, in accordance with at least some embodiments of the present invention. In this embodiment, the amplifier box 310 may be fastened to the thigh of a patient using a sterilizable belt. The sterlizable belt may be secured by a sterilizable steel belt-buckle piece. Other fastening devices and securing means may be used. Similarly, the amplifier box 310 may be fastened at a different location on the patient or in close proximity to the patient, for example, on a medical bed or nightstand.

According to one embodiment, the amplifier box 310 may include an input wire in connection with the medical device 302 and an output wire in connection with the data processor 304. Alternatively, data may be communicated into and out of the amplifier box 310 wirelessly.

According to another embodiment, the amplifier box 310 may be designed to fit comfortably around a patient's thigh or other body location. For example, the amplifier box 310 may have the approximate dimensions of 3 inches by 3.25 inches. Similarly, as shown in FIG. 7D, the sterilizable belt or other fastening device may include extra padding at the skin surface for additional comfort to the patient.

Figure 8:
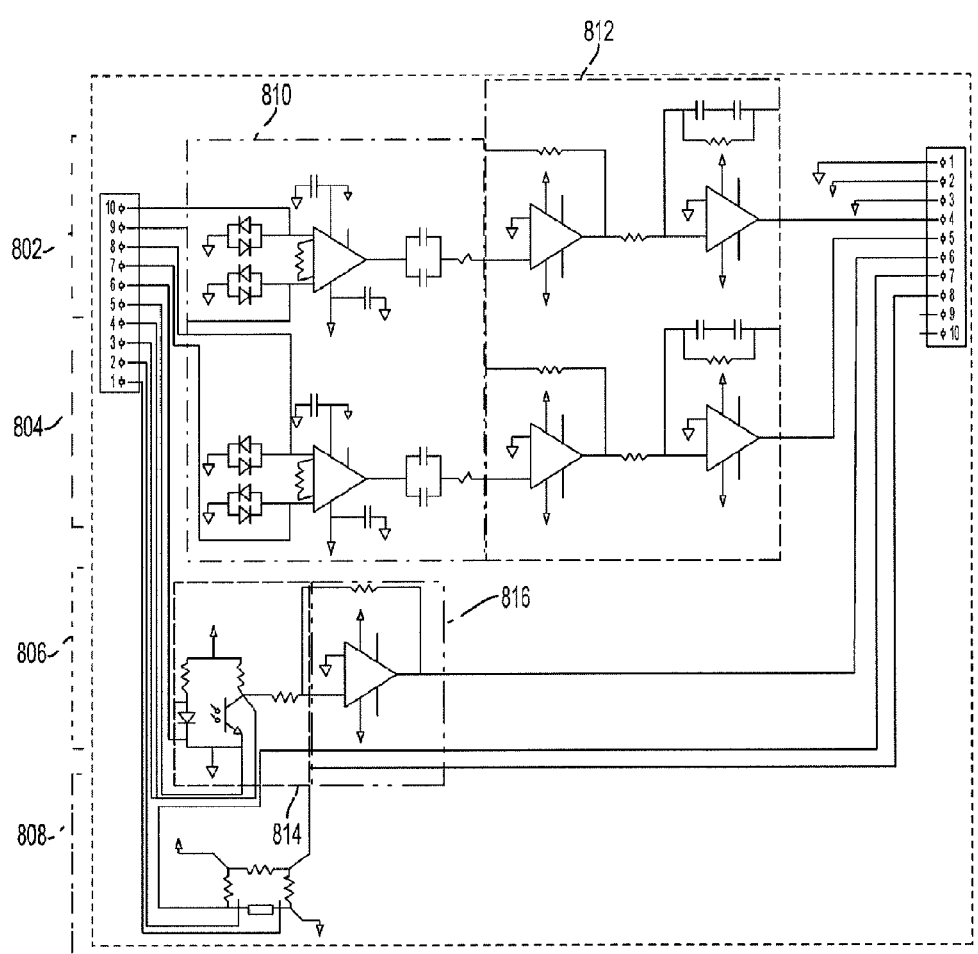
FIG. 8 is a circuit diagram of the amplifier box, in accordance with at least some embodiments of the present invention.

FIG. 8 is a circuit diagram of the amplifier box, in accordance with at least some embodiments of the present invention. The amplifier box 310 may be adapted to receive signals from each of the electrodes and sensors of the medical device 302, to amplify and reduce noise in the signals, and to output the signals to the data processor 304. The amplifier box 310 may be housed within the data processing unit 304 or may be housed in a separate component in communication with the data processing unit 304, as shown in FIGS. 7C and 7D. The circuitry may be in communication with the medical device 302 and the data processor 304 wirelessly or via hardwire. In an alternative embodiment, such filtering and signal processing may be done by software.

In FIG. 8, sections 802, 804, 808 and 810 show the communication connection between the electrodes and sensors of the medical device 302 and the circuitry. For example, section 802 of the circuit diagram indicates the circuitry adapted to receive a signal from the cervical electrodes. Section 804 indicates the circuitry adapted to receive a signal from the vaginal electrodes. Sections 806 and 808 indicate the circuitry adapted to receive signals from the light sensors and the stretch sensors, respectively.

FIG. 8 identifies amplifier and band pass circuitry using blocks 810, 812, 814 and 816. Block 810 identifies amplification circuitry that can be further adapted by instrumentation amplifiers to amplify electrode signals with high common-mode rejection ratio (CMRR). Block 812 identifies band pass circuitry adapted to reduce noise in the electrode signals and smooth the output signal. Further, blocks 814 and 816 identify amplification circuitry adapted to amplify the signals received from light sensors. The circuitry may output the amplified and noise-reduced electrode and sensor signals to the data processor 304.

Figure 9:
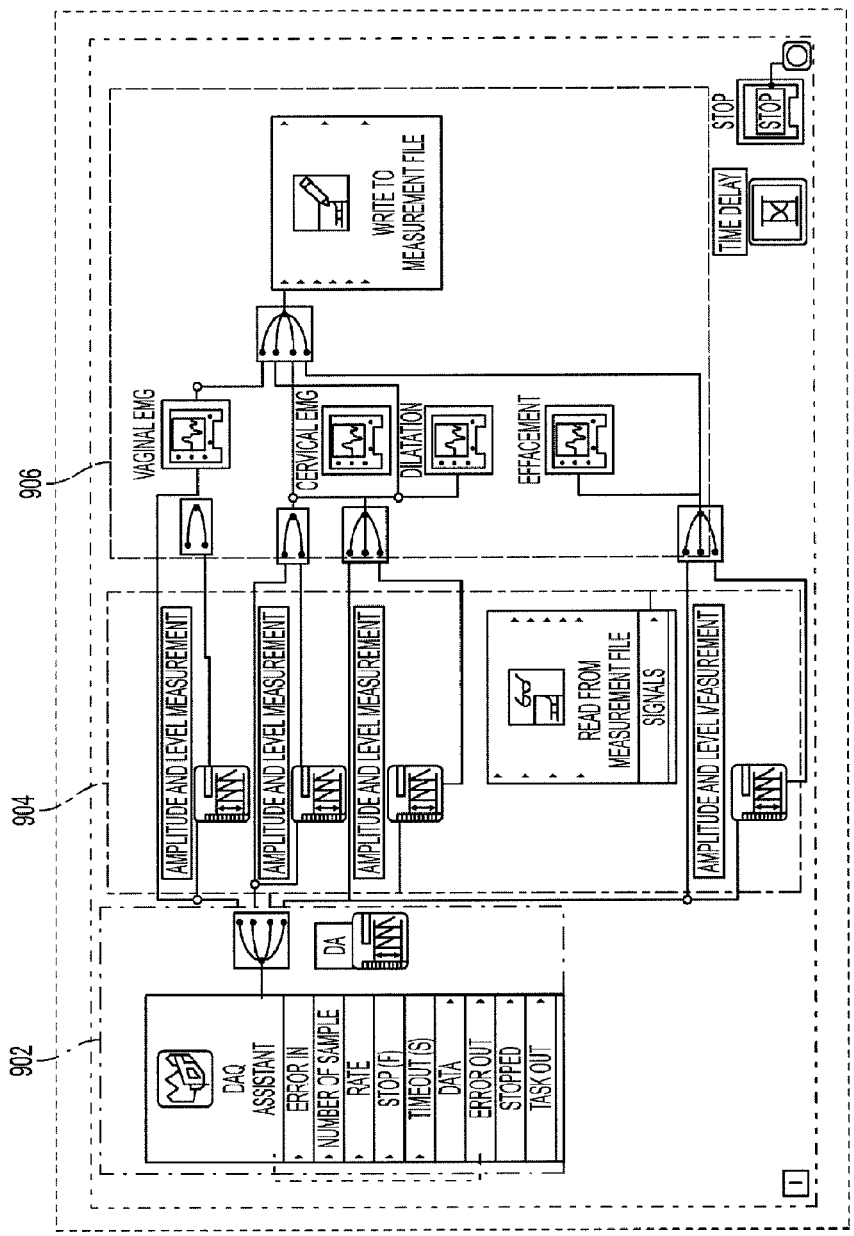
FIG. 9 is a software diagram of the data processor, in accordance with at least some embodiments of the present invention.

FIG. 9 is a software diagram of the data processor, in accordance with at least some embodiments of the present invention. Block 902 of the software diagram shows Data Acquisition Assistant software adapted to sample and filter input signals received from the medical device 302. The Data Acquisition Assistant may perform various functions, including selecting the number of data values to sample. Block 904 shows software adapted to process signals to evaluate peak amplitude. Block 906 shows software adapted to save received data in serial text-based format. The software may further determine the magnitude of cervical changes for normalization based on previous exams and/or may link archived cervical information with current cervical measurements.

According to one embodiment, the data processor may be adapted to analyze the electrical activity of the first and second electrodes 104, 106 using vector hysterography (VHG). While vectors are an indispensable tool in physics and engineering, vectors have proven its usefulness in medicine as well with the advent of electrocardiography.

Living resting cells have an electrical double layer along their membranes, the positive charge along the external surface and the negative charge along the internal surface, creating what is known as an electric potential. Generally, a cell's resting state electric potential is negative. Depolarization (becoming more positive) and repolarization (returning back to resting state) of individual cells are the changes in the difference of these electrical charges across the cell membrane from the cell resting potential. Generally, these deviations are caused by the initiation of an action potential, presence of new molecules, or an electrical change in the environment. It is the polarization and depolarization of the cell membrane that moves electrical signals along tissues and organs, such as the uterus. Action potentials propagate rapidly throughout these organs and in the uterus, initiating movement of calcium into the cell via voltage-dependent channels, which activate myofilaments and generate the electromotive force. The force produced in a contraction is known to be caused by synchronization of multiple cells, the stimulation of their calcium gated ion channels, and the culmination of their myometrial activity.

In VHG, differences between the positive deflections and the negative deflections to the set of current measuring electrodes at the point of measurement may be plotted as a wave. The units on the axes are arbitrary, dependent on the position of the electrodes and the surface of contact. The length of the vector represents the mean electromotive force, while the angle between the vector and the zero-line represents the mean direction and the sense of the vector. This construction is based on vector addition. It is assumed that the mean electromotive force of the uterus is projected in the presence of at least two current measuring electrodes and the electrical axis may be constructed from this projection using vector addition. A derived vector may represent the projection of the true spatial vector upon a plane which is parallel to the surface of measurement.

The electrical axis at any given instant during a uterine contraction is continually changing in direction and magnitude and is called the instantaneous electrical axis. The instantaneous electrical axis of the whole uterus is a vector sum, the sum of the instantaneous electrical axes generated by the polarization and depolarization of the different parts of the uterus. The instantaneous electrical axis can be seen as an electric current, measurable by electrodes, indicative of the electromotive force. An electromotive force is a vector. Thus, what is detected by VHG may be considered waves of the uterus as depolarization and repolarization waves. Although linked to the initial action potential that initiated the chain of depolarization and repolarization of individual cells, VHG may provide a macroscopic view of the uterus by measuring the instantaneous electrical axis of the entire uterus, and not one cell or muscle fiber, relative to the plane of measurement.

According to one embodiment, the medical device 100 may apply at least one electric current measuring electrode to an abdominal, vaginal or cervical surface on a patient. The data processor may process and store the electrical conductivity signal of the uterus, including the wave-front of electrical depolarization and repolarization, produced by the electrodes. Uterine activity may be analyzed using parameters indicated from the wave.

According to another embodiment, the medical device 100 may apply a current measuring, multi-polar arrangement of electrodes to the surface of a patient, including the cervical or vaginal surface. The data processor may process and store the time variation of a uterine electrical potential, detected by the electrodes. Alternatively, the data processor may process and store the spatial variation of the uterine electrophysiological potential over time with the electrodes. The data processor may analyze the uterine electrical potential and may display the uterine electrical potential in the form of a vector wave trace. The data processor may characterize the uterine contractility or electrical activity of the patient based on the analysis of the vector wave trace components.

According to a further embodiment, the medical device 100 may apply two or more electrical potential measuring electrodes to the surface of a patient, including the vaginal, abdominal or cervical surface. The data processor may process and store the time variation of a uterine electrical potential, produced by the electrodes. The data processor may display the uterine electrical potential in the form of a wave trace (See FIGS. 12-15).

According to one embodiment, the data processor using VHG may perform one or more of the following steps: 1) diagnosing labor, or the onset of labor, as a function of the parameter analysis; 2) calculating the amplitude of the potential vector in a stored signal; 3) comparing the calculated amplitude to a predetermine threshold; 4) calculating the frequency of the potential vector in the stored signals; 5) comparing the calculated frequency to a predetermined threshold; 6) calculating a rise time of a vector within said stored signal; 7) calculating the rate of rise of at least one of said vectors; 8) calculating a fall time of a vector within said stored signal; 9) calculating the rate of fall of at least one of said vectors: 10) examining one or more trends in uterine activity indicated parameters over time; and 11) displaying one or more trends in uterine activity indicated parameters over time.

Figure 10:
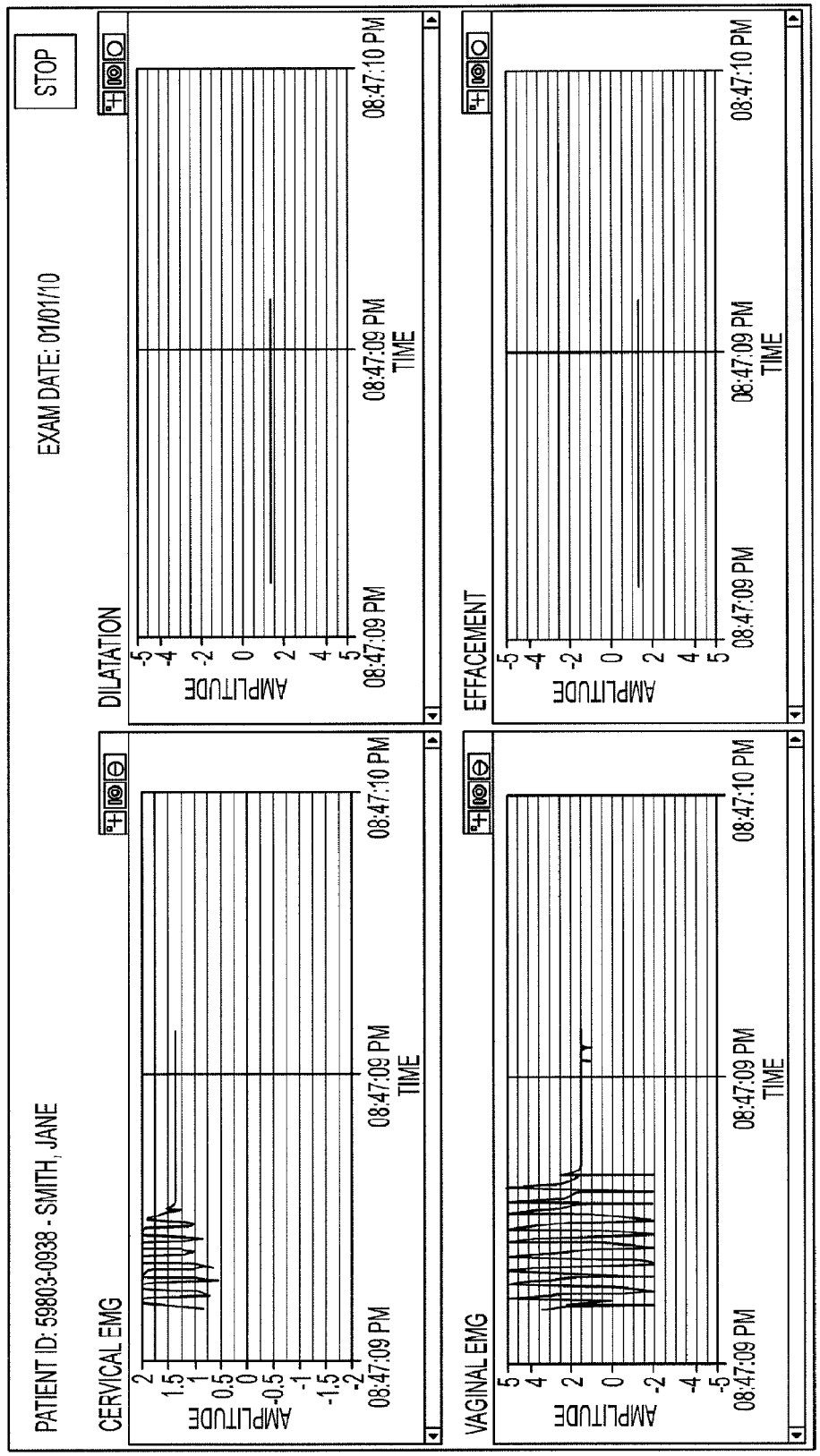
FIG. 10 shows an example of signal data on an external display, in accordance with at least some embodiments of the present invention.

FIG. 10 is a schematic illustration of an external display in communication with the data processor, in accordance with at least some embodiments of the present invention. According to one embodiment, the data processor may process signal data into a smoothed and relevant signal for optimal diagnostic value and then transfer to and display through an external monitor. The outputs that address these inputs may be realized through additional signal processing and smoothing in the software. The data may then be transferred into a graphical display on an external monitor. As an example, the device processing and display may be done through a NI External Touch Screen monitor. Data may be communicated through any one of wireless, fiber optic, memory, hardwire, etc. The external display may convey information related to the data collected from each of the cervical electrodes, the vaginal electrodes, the light sensors and the stretch sensors. According to one embodiment, a method of monitoring uterine and/or cervical activity indicative of labor in a patient includes the following steps: A medical device 302 is positioned within a patient, where a structural component 102 of the medical device 302 is arranged to be in contact with a cervical surface 118 and a vaginal surface 120 of the patient. A first electrode 104 attached to the structural component 102 receives an electrical activity of the cervical surface 118. A second electrode 106 attached to the structural component 102 receives an electrical activity of the uterus through the vaginal surface 120. A data processor 304 processes the electrical activity of the cervical and vaginal surfaces using a data processor to detect contractions of the uterus indicative of labor.

According to a different embodiment, the method for measuring contractions may include the steps of measuring cervical electrical potential directly from the cervical wall, measuring vaginal electrical potential from the vaginal wall, and extrapolating the data from the cervical and vaginal potentials to determine the changes in uterine contractility and the presence of uterine contractions.

Figure 12:
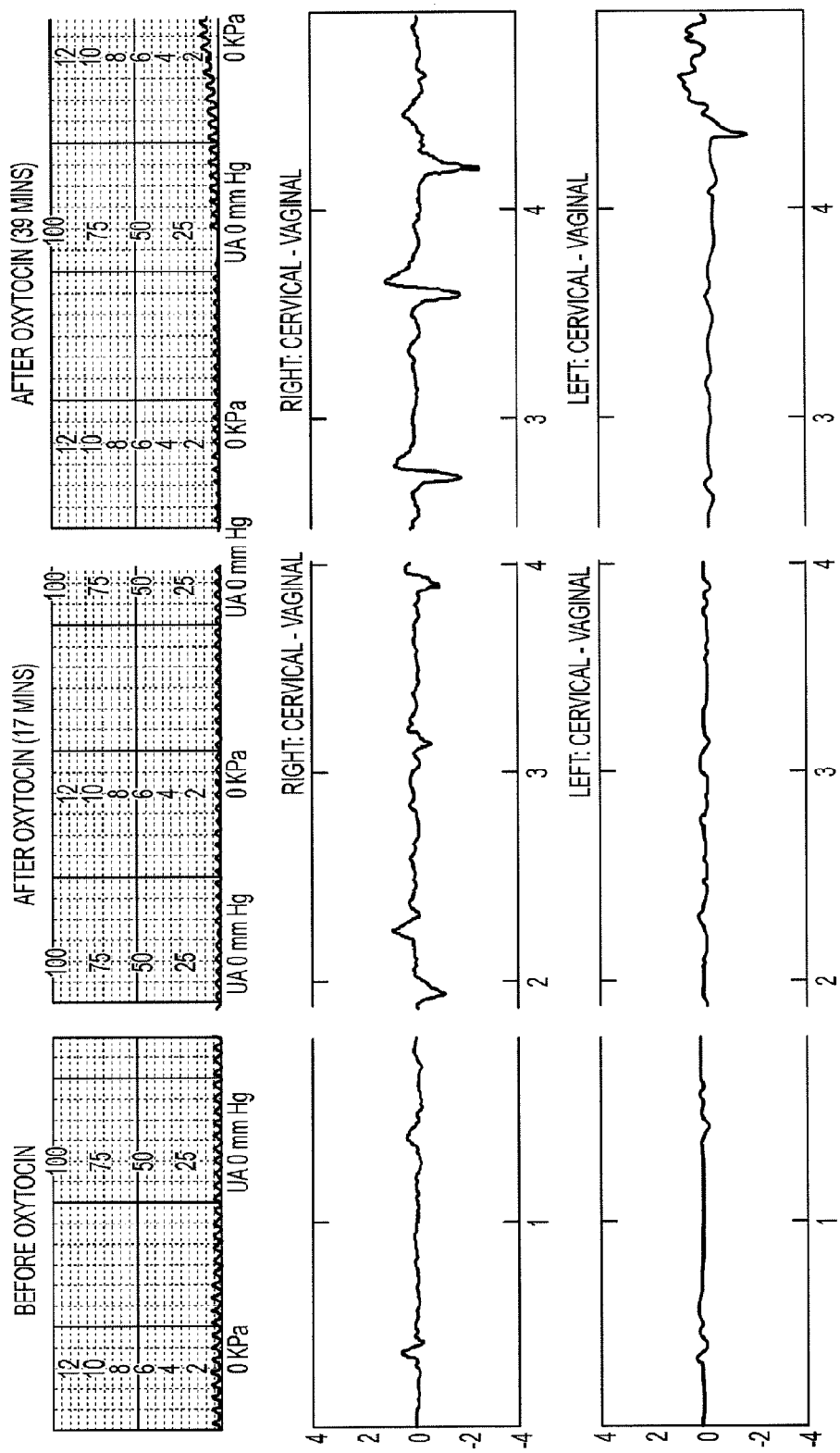
FIGS. 12-15 show comparison charts of measured data from exemplary cervical and vaginal surfaces, in accordance with at least some embodiments of the present invention.
Figure 13:
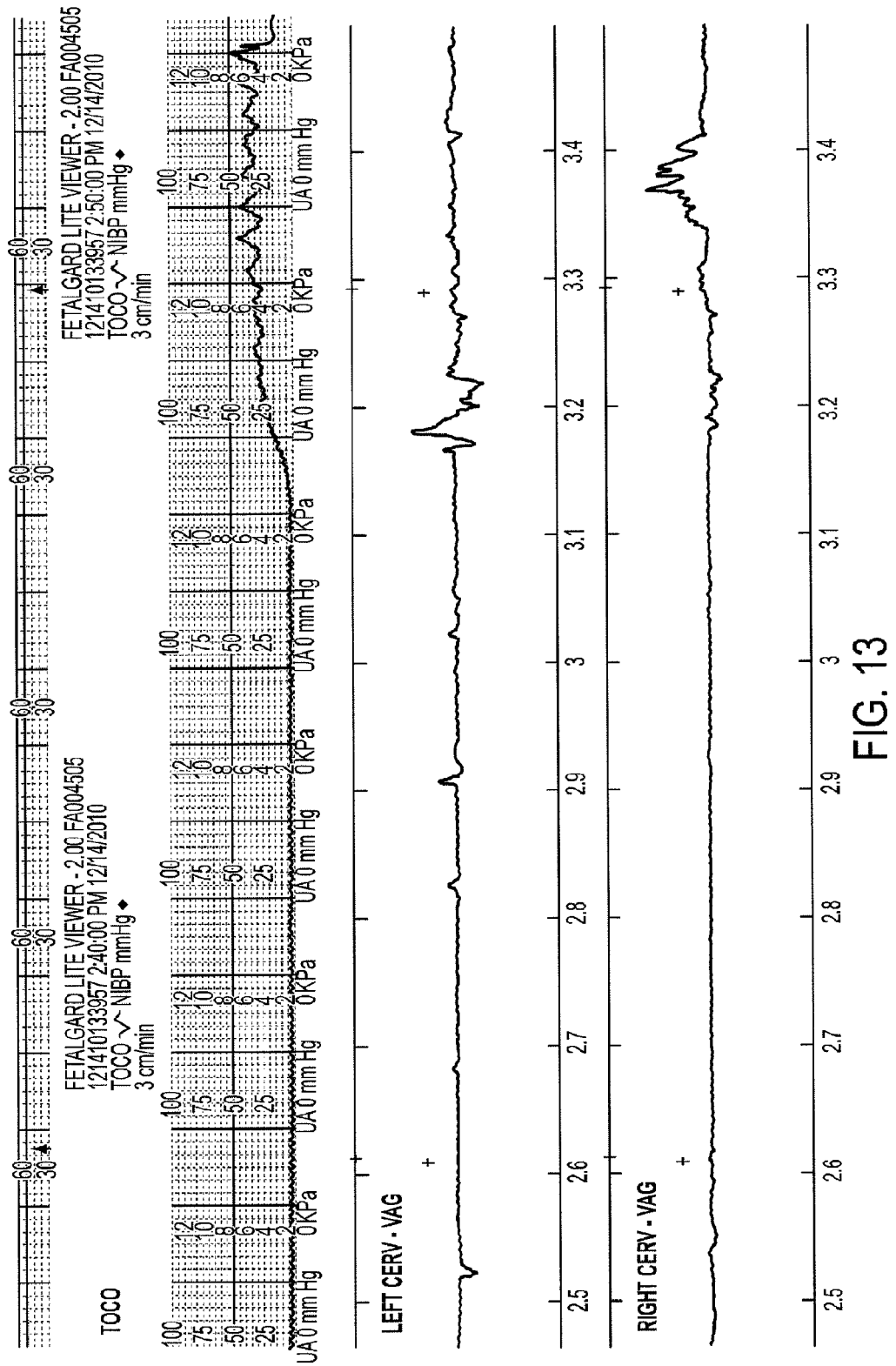
Figure 14:
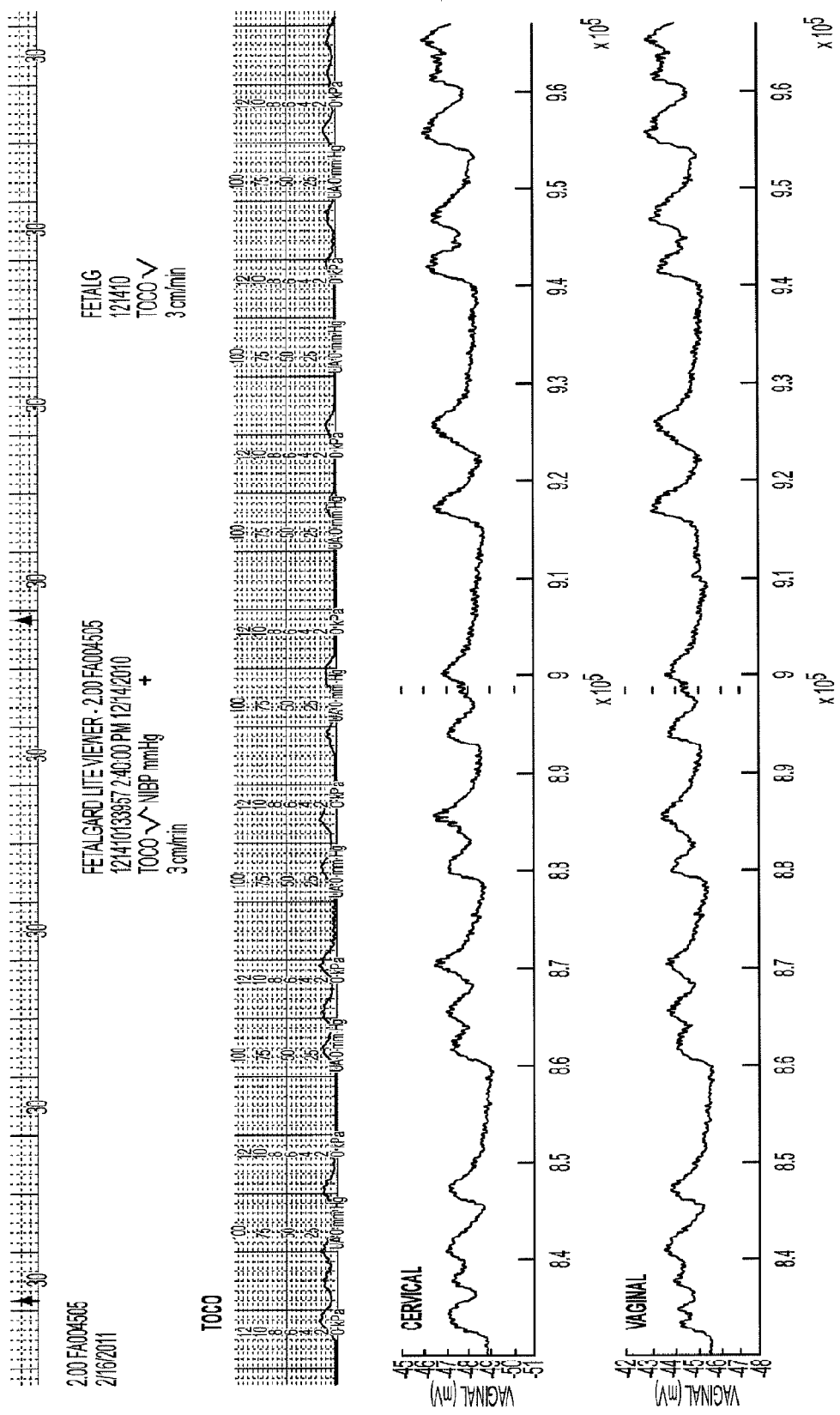

FIGS. 12-15 show comparison charts of measured data from exemplary cervical and vaginal surfaces, in accordance with at least some embodiments of the present invention. The embodiment of FIG. 12 shows a segment of data taken before injecting oxytocin, a hormone that is released in large amounts after distension of the cervix and uterus during labor, a segment of data taken 17 minutes after injecting oxytocin and a segment of data taken 39 minutes after the injection. The top graph depicts measurements taken using a tocodynamometer (TOCO), a method commonly used in the art, the middle graph depicts measurements taken between left cervical and vaginal electrodes using VHG analysis, and the bottom graph depicts measurements taken between right cervical and vaginal electrodes using VHG analysis. The middle and bottom graphs of FIG. 12, both using VHG analysis, show the clear progression and increase in signal amplitude from a period prior to oxytocin injection through a period 39 minutes after injection. Dissimilarly, the signal from the TOCO shows a much slower and less-noticeable reaction to the oxytocin injection in the patient. Similar results are shown in FIG. 13. The embodiment shown in FIG. 14 shows the alignment of measured activity between the TOCO and VHG.

Figure 15:
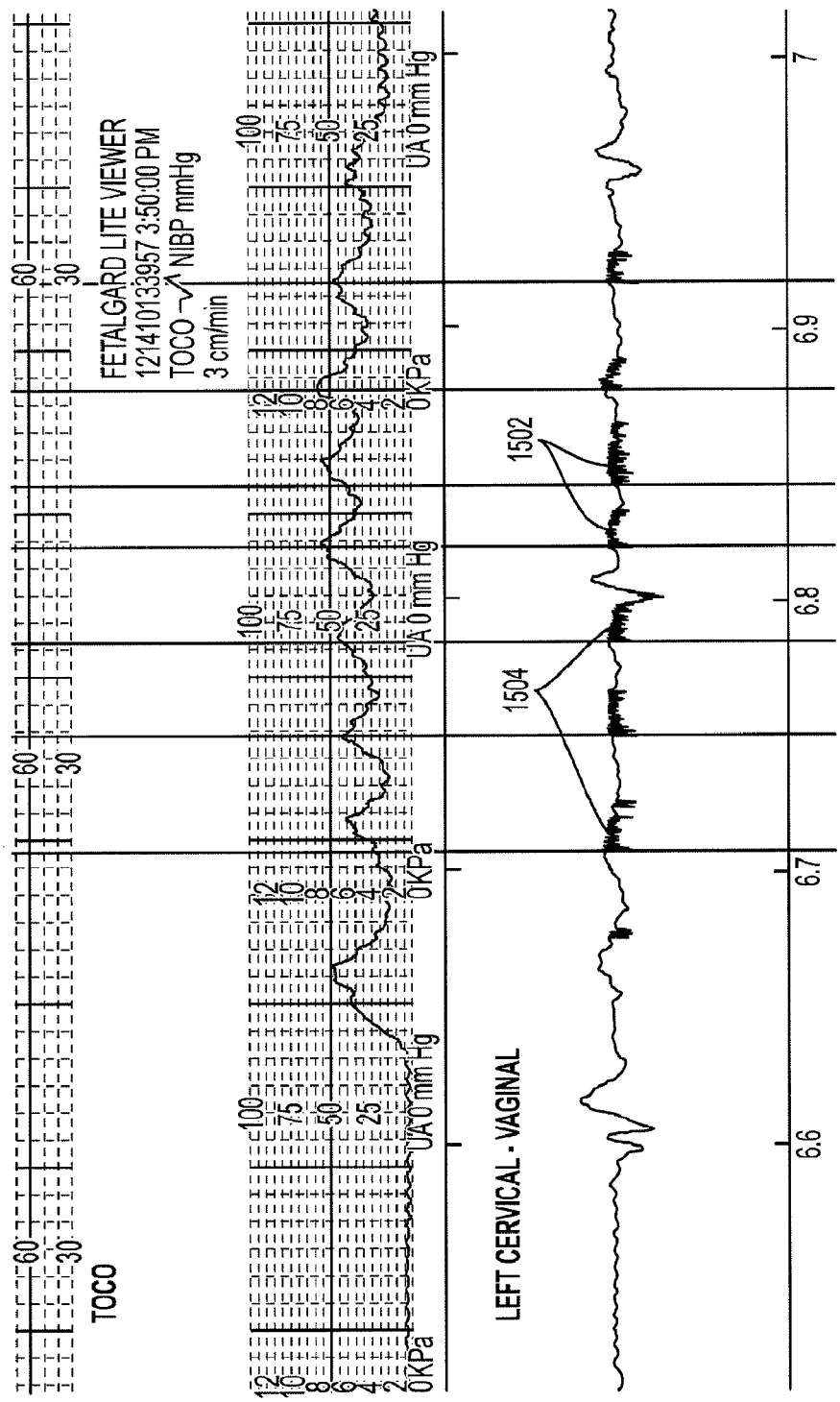

The embodiment shown in FIG. 15 shows differences in measured data from exemplary cervical and vaginal surfaces using EMG and VHG methods. The high frequency bursts 1502 are EMG bursts and the small undulations 1504 are VHG signals. FIG. 15 shows that the undulations 1504 in VHG coincide with the signal from TOCO and EMG bursts 1502 happen at the peaks of the VHG waves. In VHG analysis, the electrical signals in tissues are sum of action potentials being triggered in each cell of a tissue. As the action potentials fire from each cell and travel down the uterus in a wave, the wave is what is picked up by the electrodes and called VHG. Right when the wave of action potentials is directly under an electrode, however, the electrode essentially becomes an EMG electrode and picks up the high frequency bursts 1502 of the action potentials.

According to one embodiment, the system and method of the current invention may be used to monitor uterine activity indicative of early preterm labor with increased accuracy through direct application to the cervix. The system and method may measure and monitor the progression of uterine activity to identify cervical characteristics, dilatation and effacement, and therefore more accurately identify preterm labor. The system and method may also process the monitored data to assist in clinical diagnosis of preterm labor or pathologic and/or excessive uterine activity at any time during gestation.

Example 1

Use of Medical Device with a Patient

According to one embodiment, the medical device 100, 200, 302 may be adapted to be applied directly to the cervix by the clinician. For example, when a symptomatic or high-risk patient visits her physician for a weekly or bi-weekly routine check-up, she may undergo a series of tests, including monitoring via a tocodynamometer, a digital examination and/or a transvaginal ultrasound to assess cervical length. This evaluation can last from two hours to 24 hours while the woman is probed and monitored. The disposable cervical elastic ring portion of the medical device may be placed on the cervix of the patient after the initial digital examination, and remain for the full duration of the observation period. This may allow the physician to closely monitor the patient's dilatation, effacement, and contractions without constantly being in attendance. The readings may be provided by a separate monitor and saved to a hard-drive. At each evaluation for preterm labor, the patient may be provided with a new pre-sterilized cervical ring device. Aside from the placement of the device, there will be no additional work for the physician other than to plug-and-monitor. After the evaluation, the disposable medical device 100 can be discarded and the patient billed for the use of the device.

The device may be developed to fit directly into the current care pathway, allowing for quick adoption into existing obstetric practices. The initial target market for this device may include patients with known risk factors for preterm labor because they already undergo increased monitoring and would benefit most from an accurate monitoring device. By maintaining familiar display settings and simplified operation methods, the device may easily be used by physicians in all pregnancies and may potentially replace current labor activity monitoring devices.

Example 2

Direct Application to the Cervix

According to an embodiment, the medical device 100, 200, 302 may be comprised of flexible, biocompatible and sterilizable components that conform to a normal pregnant cervix. The outputs that address these inputs may be realized in the design of the cervical ring through the specified characteristics of materials, fixation points and overall form factor.

According to one embodiment, the elastic ring 108 may have an initial inner diameter of approximately 20 mm and a stretched inner diameter of approximately 40 mm. The flexible band may have a thickness of approximately 4 mm and a depth of approximately 10 mm. Each wing portion may have a width of approximately 10 mm and a depth of approximately 7 mm.

According to another embodiment, the device may be made of biocompatible medical grade polymer, for example, but not limited to, a medical grade silicone elastomer. The optimal Young's modulus, sometimes referred to as the elastic modulus or modulus of elasticity, may be approximately 1,500 to 15,000 psi. The tensile strength of the device may maintain fixation and contact with the interior surface region of the patient. Examples of such material are 1) MED-4025 silicone elastomer by NuSil[2], which has a tensile strength of 1272 psi, and 2) MED-4920 silicone elastomer by NuSil[2], which has a tensile strength of 1032 psi. Both materials have passed cytotoxicity testing and are adapted towards transfer/compression molding. It has been found, however, that silicone rubber is not approved for internal human use.

Example 3

Direct Detection of Cervical/Uterine Activity

According to one embodiment, the medical device 100, 200, 302 may be comprised of uterine contractility sensors (measuring cervical and vaginal electrical potential), effacement sensors (measuring tissue thickness) and dilatation sensors (measuring diameter). The outputs that address these inputs are realized in the selection of the cervical ring sensors through the specified characteristics and placement of the selected electrodes, LED emitter and detector pair and embedded stretch gauge.

According to another embodiment, unipolar electrodes may be used to detect both cervical and uterine contractions and/or electric potentials. Such electrodes may be made from, for example, 316L stainless steel and/or sintered silver chloride (Ag—AgCl). The electrodes may have an approximately 8 mm diameter. According to one embodiment, the electrodes may comprise EMG electrodes having a measurement range of approximately 50 to 3000 Hertz. According to a different embodiment, the electrodes may comprise biocompatible electrodes having a measurement range of approximately 0.001 to 0.5 Hertz and may be used for VHG applications. Alternatively, piezoelectric, fetal fibronectin and spring force sensors may be used to detect cervical and uterine contractions.

According to a further embodiment, a vaginal electrode may obtain a signal through contact with the vaginal surface with respect to a reference signal. The cervical electrode may obtain a signal through contact with the cervical surface with respect to a reference signal. The reference signal may be taken at the inner thigh of the patient.

According to another embodiment, light sensors may be used to determine the tissue thickness of the cervical or vaginal surface by obtaining a signal through light reflectance measurement from the surface. The light sensor may be less than 1.5 cm by 1.5 cm and may have a measurement range of 950 nm. According to an alternative embodiment, the light sensor may test the collagen of the blood in the surface tissue to determine efficacy (i.e. the shortening or thinning of the surface tissue). The light sensor may comprise one of a UV light emitter, an infrared light emitter or an LED light emitter. Similarly, the light sensor may utilize impedance, auto-florescence, ultrasound or reflection to detect tissue thickness of the cervical surface.

According to another embodiment, a stretch gauge may be used to determine the dilatation of the cervical surface. The stretch gauge may have, for example, a 7.5 mm radius and may measure approximately 1-2 K'Ω per linear inch. The stretch gauge may be placed directly around the circumference of the cervix. Alternatively, an ultrasound may be used to determine dilatation.

Example 4

Special Considerations on Electrode Placement

According to one embodiment, the medical device 100, 200, 302 may include only one set of electrodes placed on the inner surface of the cervical ring. However, the inclusion of additional electrodes may improve the resulting acquired signal. For example, the medical device may include two additional electrodes attached at the tips of the wing protrusions of the cervical ring to pick up uterine contractions from the upper vaginal walls.

There are two main phases of cervical activity: a latent phase and an active phase. A latent phase includes both synchronous bursts and asynchronous bursts. Synchronous bursts are a contraction response to an electrically-active uterus. Asynchronous bursts are generated by smooth muscles of an unripe cervix. In the active phase, the cervical electrical activity is reduced. Electrical activity of the cervix in the active phase is synchronous with uterine activity (i.e. the dominant force) and is indicative of effacement (restructuring) and dilation. Considering the behavior of the cervix in these two main phases, the value of additional vaginal and/or uterine electrodes lies not only in the strengthening of the data but also in its possible contributions to a more specific understanding of electrical activity as it travels from the uterus to the cervix during labor.

Example 5

Real-Time Monitoring and Signal Processing

According to one embodiment, multiple design inputs may be established requiring the device to optimally amplify and filter the acquired signals to provide the most useful and accurate information to the operating clinician. The outputs that address these inputs are realized in the development of the signal amplification circuitry, noise filtering band pass circuitry, and signal processing software.

For example, the system may utilize TI INA128P instrumentation amplifiers on all of the acquired signals. The acquired signals may then each be filtered through band pass circuitry built from LN741 CN op amps. These signals may then be processed using National Instruments LabView software in order to smooth the signal for post-processing display and save the obtained data for diagnostic reference and signal normalization. The current circuit and software diagrams are illustrated in FIGS. 8 and 9, respectively.

For amplification of the acquired signals, the circuit may utilize TI INA128P instrumentation amplifiers with a gain of 3000 and CMRR of 120. Although these amplifiers have been sufficient to pickup and display electrical signals from forearm muscle contractions, cervical and uterine electrical activity will be of much smaller magnitude and likely accompanied by various signal noise from the measurement environment. Thus, commercially available amplifiers, such as the CleveMed BioRadio, may also be used. Alternatively, the signal may be outsourced to a professional grade EMG amplifier built to the device's particular specifications.

In addition to amplification concerns, it is important to consider how the transmission of low-magnitude cervical and uterine electrical signals into the signal processing and filtering could be affected by signal-wire cross-talk. According to one embodiment, the circuit may utilize shielded wiring as well as twisted ground pair wiring schemes to limit cross-talk effects on signal propagation.

Example 6

Additional Design Considerations and Constraints

The following represent other design considerations for the medical device 100, including those of maintenance, compatibility, sterilization, regulatory requirements and labeling. For example, the medical device may be adapted to withstand a three-foot fall and impact with concrete, wood or tile surface. The medical device may be adapted not to interfere with digital exams intended to measure cervical changes. The medical device 100 may also be adapted to be able to withstand in-package gamma ray sterilization before use without degrading or losing electrical signal function.

The medical device may be adapted to follow all medical design controls, including software control and verification, as well as validation of all design inputs and outputs. The medical device may also include instructions written to an $8^{th}$ grade reading level. The medical device may further accommodate human factors, such as providing a cervical ring that is colored to provide a patient options such as choice of pink, blue or a gender-neutral color like green.

In addition to these design goals, the following important constraints may be considered in the design of the system: 1) may not harm or damage mother and/or fetus; 2) may not cause any degree of cervical necrosis; 3) may not easily slip or fall away from cervix; 4) may not induce preterm labor; 5) may not contain Latex material; and 6) may not impede natural fluid flow.

Example 7

Verification of Design Outputs

According to one embodiment, the medical device 100, 200, 302 may be adapted towards the optimal materials and mixture ratio, the form for improved fixation and sensor placement, and flexible shielded wiring. For example, the form factor materials used in the medical device may satisfy the input requirements of flexibility and sterilization, as has been determined through documentation and force measurements. The material may also be verified for biocompatibility. For example, the medical device may comprise biocompatible and sterilizable materials made from a silicone elastomer.

Similarly, the form factor shape of the medical device may be designed for optimal fixation and sensor placement in the target signal acquisition space. The basic design placement, as shown in FIGS. 3 and 4, has been initially verified using anatomy simulation models and confirmed by leading clinicians. For example, the medical device may be adapted for optimal fixation in the target signal acquisition space using the following alternatives: memory foam, a cup with a hole, an inflatable balloon, a donut shaped balloon having a "U" shape, a claw with a spring, calipers and/or a spring sensor. The method of fixation may include spring force, a clip to the cervical wall, a screw hook, memory foam, an inflatable balloon (donut) and/or hydrogel.

According to a further embodiment, the sensors of the medical device may be integrated into the device to specifically and efficiently receive the desired cervical and uterine activity. For example, the dilatation stretch gauge may be used in the device to pick up small changes in tension when applied to the gauge. In another example, the medical device may include effacement sensors. Here, a UV light emitter/detector pair may be approved for biologic applications such as oximeter measurements. Alternatively, LED light emitters and/or infrared light emitters may be used. According to a further example, stainless-steel EMG sensors may be used in the device to accurately pick up muscle contractions. The high-cost of these sensors has led to custom built steel electrodes, which, once fabricated, may be used to pick up contractions safely in vivo.

According to one embodiment, the signal amplification in the medical device may use both commercially available amplifiers and outsourced fabricated amplifiers to accommodate the low order-of-magnitude electrical signals of the targeted cervical and vaginal surfaces. In addition to basic amplification verification, the medical device 100 may limit potential crosstalk and use lubricating jelly, as described above. Further, software may be used at the data processor to reduce noise and common-mode rejection ratio (CMRR) of the signals, to optimize frequency filter and signal processing and to upgrade data acquisition (DAQ) sampling.

According to another embodiment, the data processor may transmit signal information to an external display. An example user interface may be provided using NI LabView software and the NI Industrial Touch Screen Monitor, as discussed above. The display may include human factors (such as the name of the patient) and a user interface to be used during in-clinic testing. Additionally, the fetal heart rate may be shown on the external display.

Example 8

Alternative Uses of the Medical Device

As described above, the medical device 100, 200, 302 may be used for preterm labor detection. The device may be configured to detect any combination of contractions, effacement and dilatation.

Additional uses of the medical device include combination with fetal heart rate monitoring, chronic pelvic pain applications, monitoring of full term obese pregnant women, or monitoring of any pregnancy to obtain more accurate uterine contraction information. For example, the medical device may be used to diagnose chronic pelvic pain in non-pregnant women, as some chronic pelvic pain is derived from uterine contractions, such as menstrual cramps. It can also be used in patients less than 20 weeks' gestation to determine if increased uterine activity is present and avoid unnecessary placement of a cerclage for an erroneous diagnosis of cervical incompetence.

The embodiments illustrated and discussed in this specification are intended only to teach those skilled in the art the best way known to the inventors to make and use the invention. In describing embodiments of the invention, specific terminology is employed for the sake of clarity. However, the invention is not intended to be limited to the specific terminology so selected. The above-described embodiments of the invention may be modified or varied, without departing from the invention, as appreciated by those skilled in the art in light of the above teachings. It is therefore to be understood that, within the scope of the claims and their equivalents, the invention may be practiced otherwise than as specifically described.

We claim:

1. A medical device for monitoring uterine and/or cervical activity indicative of uterine activity in a patient, comprising:
   a structural component;
   a first electrode attached to the structural component; and
   a second electrode attached to the structural component,
   wherein the structural component is structured to be arranged in contact with a cervical surface and a vaginal surface of the patient such that said first electrode is in electrical contact with said cervical surface and said second electrode is in electrical contact with said vaginal surface,
   wherein the first electrode is adapted to receive an electrical activity of said cervical surface, and
   wherein the second electrode is adapted to receive an electrical activity of the uterus through said vaginal surface.

2. The medical device of claim 1, wherein the structural component comprises an elastic ring defining a hollow center that is suitable to be arranged in contact with the cervical surface, and wherein the first electrode is positioned on an interior portion of the elastic ring.

3. The medical device of claim 2, wherein the structural component further comprises a projecting portion coupled to the elastic ring, wherein the projecting portion is suitable to be arranged in contact with the vaginal surface, and wherein the second electrode is positioned on the projecting portion.

4. The medical device of claim 2, further comprising a plurality of projecting portions coupled to the elastic ring, wherein the projecting portions are suitable to be arranged in contact with the vaginal surface, and wherein the second electrode is coupled to one of the projecting portions and an additional electrode is coupled to each of the other projecting portions.

5. The medical device of claim 1, further comprising a stretch sensor attached to the structural component and arranged to detect a change in resistance in response to contractions and dilations of the cervical surface of the patient.

6. The medical device of claim 1, further comprising a light sensor attached to the structural component that is adapted to measure changes in reflectance of light from the cervical surface of the patient.

7. The medical device of claim 6, wherein the light sensor comprises at least one light-emitting diode element.

8. The medical device of claim 1, further comprising:
   a stretch sensor attached to the structural component and arranged to detect a change in resistance in response to contractions and dilations of the cervical surface of the patient; and
   a light sensor attached to the structural component that is adapted to measure changes in reflectance of light from the cervical surface of the patient.

* * * * *